United States Patent
Fibi et al.

(10) Patent No.: US 6,673,609 B1
(45) Date of Patent: Jan. 6, 2004

(54) RECOMBINANT HUMAN ERYTHROPOIETIN WITH ADVANTAGEOUS GLYCOSYLATION PROFILE

(75) Inventors: Mathias Fibi, Marburg (DE); Peter Hermentin, Marburg (DE)

(73) Assignee: Aventis Pharma Deutschland GmbH (DE)

(*) Notice: Subject to any disclaimer, the term of this patent is extended or adjusted under 35 U.S.C. 154(b) by 0 days.

(21) Appl. No.: 09/486,222

(22) PCT Filed: Aug. 26, 1998

(86) PCT No.: PCT/EP98/05399

§ 371 (c)(1),
(2), (4) Date: Feb. 24, 2000

(87) PCT Pub. No.: WO99/11781

PCT Pub. Date: Mar. 11, 1999

(30) Foreign Application Priority Data

Sep. 1, 1997 (EP) .............................. 97115081

(51) Int. Cl.[7] ........................ C12N 15/00; A61K 38/22; A61K 38/16
(52) U.S. Cl. .................... 435/440; 530/350; 514/2; 514/21; 424/198.1; 424/278.1; 536/23.1; 435/69.1; 435/320.1
(58) Field of Search .................. 530/350, 300; 514/6, 2, 21; 536/23.1; 435/69.1, 320.1, 440; 424/278.1, 198.1

(56) References Cited

U.S. PATENT DOCUMENTS 5,641,663 A * 6/1997 Garvin et al. ............. 435/172.1

FOREIGN PATENT DOCUMENTS

| EP | 0267678 | * 5/1988 | ........... C12N/15/00 |
| US | WO9505465 | * 2/1995 | ........... C12N/15/12 |
| WO | WO 9206116 | * 4/1992 | |

OTHER PUBLICATIONS

Boissel, J.-P. et al. (993) Erythropoietin structure–function relationships. Mutant proteins that test a model of tertiary structure. J. Biol. Chem. vol. 268, pp. 15983–15993.*

Higuchi, M. et al. (1992) Role of sugar chains in the expression of the biological activity of human erythropoietin. J. Biol. Chem. vol. 267, pp. 7703–7709.*

Conradt, H. S. et al. (1997) The stryctural Variety of natural glycoproteins requires the construction of novel cell factories for the biotechnological production of improved recombinant human therapeutics. pp. 1–22.*

Fibi et al.; N– and O–Glycosylation Muteins of Recombinant Human Erythropoietin Secreted From BHK–21 Cells; Blood; vol. 84, No. 5; 1995; pp. 1229–1236; XP–002053700.

Takeuchi et al.; Relationship Between Sugar Chain Structure and Biological Activity of Recombinant Human Erythropoietin Produced in Chinese Hamster Ovary Cells; Proc. Natl. Acad. Sct. USA; vol. 86; Oct. 1989; pp. 7819–7822; XP–002053701.

(List continued on next page.)

Primary Examiner—Karen Cochrane Carlson
Assistant Examiner—Samuel Wei Liu
(74) Attorney, Agent, or Firm—Heller Ehrman White and McAuliffe

(57) ABSTRACT

A method for the production of a polypeptide, the method comprising culturing, under conditions which allow for the expression of DNA encoding SEQ ID NO:2 in an eukaryotic host cell, wherein the DNA is in vector pPHOEBE-40-7, and optionally isolating the polypeptide from the culture, is described. A polypeptide obtained by such method and a pharmaceutical composition comprising the polypeptide also are described. A composition for diagnosing anemia comprising such polypeptide and a method of treating anemia caused by lack of erythropoietin also are described.

7 Claims, 2 Drawing Sheets

OTHER PUBLICATIONS

Dube et al.; Glycosylation at Specific Sites of Erythropoietin Is Essential for Biosynthesis, Secretion, and Biological Function; Journal of Biological Chemistry; vol. 263, No. 33; 1988; pp. 17516–17521; XP–002053702.

Yamaguchi et al.; Effects of Site–directed Removal of N–Glycosylation Sites in Human Erythropoietin on Its Production and Biological Properties; The Journal of Biological Chemistry; vol. 266, No. 30; 1991; pp. 20434–20439; XP–002053703.

Delorme et al.; Role of Glycosylation on the Secretion and Biological Activity of Erythropoietin; Biochemistry; 1992; pp. 9871–9876; XP–002053704.

Fibi et al.; "Inactivation of Recombinant Plasmid DNA from a Human Erythropoietin–Producing Mouse Cell Line Grown on a Large Scale"; Appl. Microbiol. Biotechnol. vol. 35; 1991; pp. 622–630; XP–002053705.

* cited by examiner

SEQUENCE LISTING

<160> NUMBER OF SEQ ID NOS: 2

<210> SEQ ID NO 1
<211> LENGTH: 166
<212> TYPE: PRT
<213> ORGANISM: Homo sapiens

<400> SEQUENCE: 1

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Arg Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Asp Arg Val
    130                 135                 140

Tyr Ile His Pro Phe Arg Gly Lys Leu Lys Leu Tyr Thr Gly Glu Ala
145                 150                 155                 160

Cys Arg Thr Gly Asp Arg
                165
```

<210> SEQ ID NO 2
<211> LENGTH: 166
<212> TYPE: PRT
<213> ORGANISM: Homo sapiens

<400> SEQUENCE: 2

```
Ala Pro Pro Arg Leu Ile Cys Asp Ser Arg Val Leu Glu Arg Tyr Leu
 1               5                  10                  15

Leu Glu Ala Lys Glu Ala Glu Gln Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Arg Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Asp Arg Val
    130                 135                 140
```

-continued

```
Tyr Ile His Pro Phe Arg Gly Lys Leu Lys Leu Tyr Thr Gly Glu Ala
145                 150                 155                 160
Cys Arg Thr Gly Asp Arg
                165
```

RECOMBINANT HUMAN ERYTHROPOIETIN WITH ADVANTAGEOUS GLYCOSYLATION PROFILE

CROSS-REFERENCE TO RELAYED APPLICATIONS

The present invention claims the benefit of PCT/EP98/05399, filed Aug. 26, 1998, which claims a priority date from EP 97115081.8, filed Sep. 1, 1997.

BACKGROUND OF THE INVENTION

1. Field of the Invention

The present invention relates to polypeptides having part or all of the primary structural conformation of erythropoietin and having an improved in vivo half-life and biological activity due to a modified glycosylation profile. The present invention also provides DNA sequences encoding the amino acid sequence of said polypeptides operatively linked to regulatory elements which allow for the expression of said DNA sequence in eukaryotic host cells as well as vectors comprising such DNA sequences. The present invention also relates to host cells comprising the aforementioned DNA sequences and vectors and their use for the production of the aforedescribed polypeptides. Furthermore, the present invention relates to pharmaceutical and diagnostic compositions comprising the aforementioned polypeptides, DNA sequences and vectors. The present invention also relates to the use of the aforedescribed polypeptides, DNA sequences and vectors for the preparation of pharmaceutical compositions for treating all kinds of anaemia caused by a lack of erythropoietin.

2. Description of the Related Art

The erythrocyte is by far the most common type of cell in the blood. When mature, it is packed full of hemoglobin and contains practically none of the usual cell organelles. In an erythrocyte of an adult mammal, even the nucleus, endoplasmic reticulum, mitochondria, and ribosomes are absent, having been extruded from the cell in the course of its development. The erythrocyte, therefore, cannot grow or divide; the only possible way of making more erythrocytes is by means of stem cells. Furthermore, erythrocytes have a limited life span of about 120 days in humans. Worn-out erythrocytes are phagocytosed and digested by macrophages in the liver and spleen, which remove more than $10^{11}$ senescent erythrocytes in every human being per day. A lack of oxygen or a shortage of erythrocytes stimulates cells in the kidney to synthesize and secrete increased amounts of erythropoietin into the blood-stream. The erythropoietin in turn stimulates the production of more erythrocytes. Since the change in the rate of release of new erythrocytes into the blood-stream is observed as early as 1 or 2 days after an increase in erythropoietin levels in the blood-stream, the hormone must act on cells that are very close precursors of the mature erythrocytes. The cells that respond to erythropoietin can be identified by culturing bone marrow cells in a semisolid matrix in the presence of erythropoietin. In a few days colonies of about 60 erythrocytes appear, each founded by a single committed erythrocyte progenitor cell. This cell is known as an erythrocyte colony-forming cell, or CFC-E, and gives rise to mature erythrocytes after about six division-cycles or less. The CFC-Es do not yet contain hemoglobin, and they are derived from an earlier type of progenitor cell whose proliferation does not depend on erythropoietin. CFC-Es themselves depend on erythropoietin for their survival as well as for proliferation: if erythropoietin is removed from the cultures, the cells rapidly undergo programmed cell death. Erythropoietin as other colony stimulating factor is a glycoprotein that acts at low concentration (about $10^{-12}$ M) by binding to specific cell-surface receptors. These receptors belong to a large receptor family, the so-called "cytokine receptor family", whose members are usually composed of two or more subunits, one of which is frequently shared among several receptor types. Mature human erythropoietin is a glycoprotein with a molecular weight of 34 to 38 kD and consists of 166 amino acids (AS) and the glycosyl residue accounts for about 40% of the molecular weight. Since erythropoietin is required for the renewal of erythrocytes, this hormone is essential for the quality of life, especially of patients, which suffer from anaemia and hypoxia, due to reduced numbers of red blood cells which can be caused by, e.g., dialysis or through reduction of erythroid precursor cells as a consequence of therapies based on the suppression of cellular proliferation or by inborne or aquired insufficiency of erythropoietin production. The identification of the human gene encoding erythropoietin made it possible to recombinantly express this protein in heterologous host cells and to provide sufficient amounts of recombinant human erythropoietin (rhuEpo) for the treatment of the diseases mentioned. However, apart from the primary structure of the protein the structure of the sugar side chains of the molecule is of particular importance for the interaction of Epo within the organism. For example, desialylated Epo shows no effect upon application in animals. It nevertheless binds to the receptor and stimulates precursor cells. The activity decrease of asialo-Epo in vivo can be explained by the fact that it is removed in the liver via receptors with a specificity for galactosyl residues which are susceptible in desialylated Epo.

The wildtype Epo, which has been used therapeutically, has in some patients the effect of increasing the blood pressure, which is disadvantageous in therapy. It is to be assumed that Epo also is integrated in the blood pressure regulation. Therefore, it is desirable to have proteins with the physiological effect of Epo at one's disposal which do, however, not show these undesired properties but which nevertheless stimulate the differentiation and division rate of precursor cells to erythrocytes. A further side effect of Epo found in some patients is the stimulation of the megakaryocytes for the formation of thrombocytes. Therefore, there is potential danger of thrombosis during the therapy with Epo, which then has to be discontinued immediately. In this case, a higher specificity of the Epo used would be desirable.

Thus, the technical problem underlying the present invention is to provide rhuEpo having an improved biological activity and in-vivo half-life compared to naturally occurring and rhuEpo so far available.

BRIEF SUMMARY OF THE INVENTION

The solution to the above technical problem is achieved by providing the embodiments characterized in the claims.

Accordingly, the invention relates to a polypeptide having part or all of the primary structural conformation of erythropoietin possessing the biological property of causing bone marrow cells to increase production of reticulocytes and red blood cells and to increase haemoglobin synthesis or iron uptake, said polypeptide being the product of eukaryotic expression of an exogenous DNA sequence and having the following physiochemical properties:

(i) the amino acid sequence comprises the amino acid sequence given in SEQ ID No. 1 or any fragment or derivative thereof by way of amino acid deletion, substitution, insertion, addition and/or replacement of the amino acid sequence given in SEQ ID No. 1, wherein at least one of the consensus N-linked glycosylation sites is modified to other than a consensus N-linked glycosylation site;

(ii) it is glycosylated;

(iii) greater 5% of the N-glycan structures are sulfated; and (iv) the ratio $Z^*$ of the total N-glycan charge Z to the number of N-glycosylation sites is greater than 170.

A. The biologic activities of different concentrations of rhuEpo wt and rhuEpo(Gln24) were tested in a human bone marrow red colony assay. GM-CSF and medium samples were coanalyzed as controls. The number of red colonies was evaluated after two weeks of cultivation for each sample.

B. The biological activities of different concentrations of rhuEpo wt and rhuEpo(Gln24) of the invention were tested in a human bone marrow red colony assay. Medium samples were coanalyzed as controls. The number of red colonies was evaluated after two weeks of cultivation for each sample.

DETAILED DESCRIPTION OF THE INVENTION

Figure 1A:
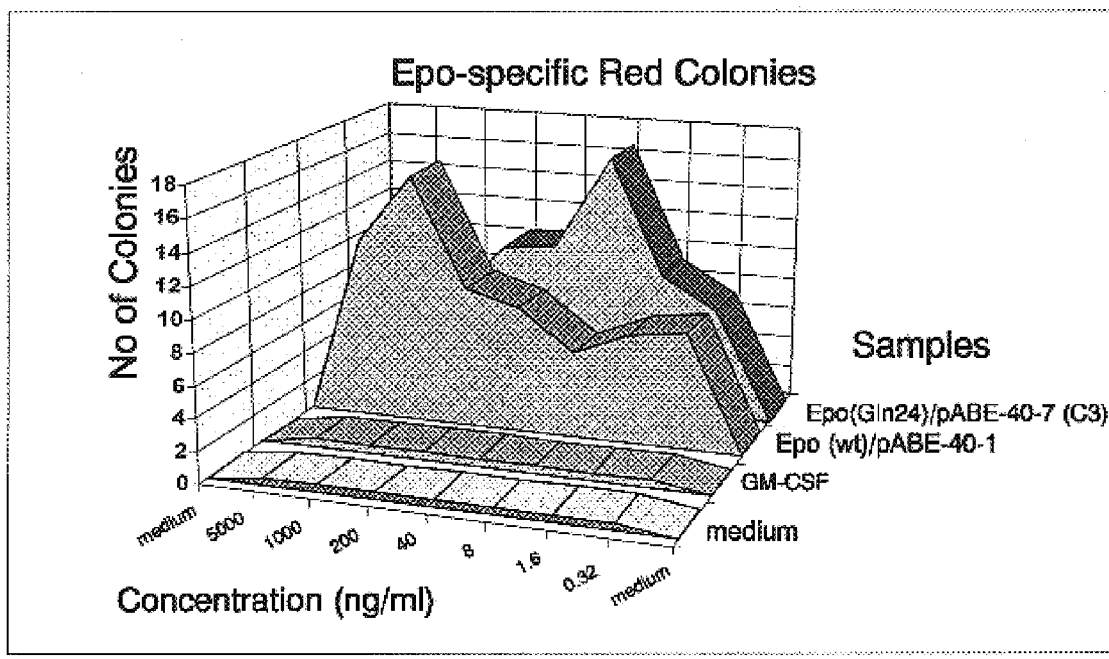
FIG. 1: Biological activity of different concentrations of rhuEpo(WT) and rhuEpo(Gln24)
Figure 1B:
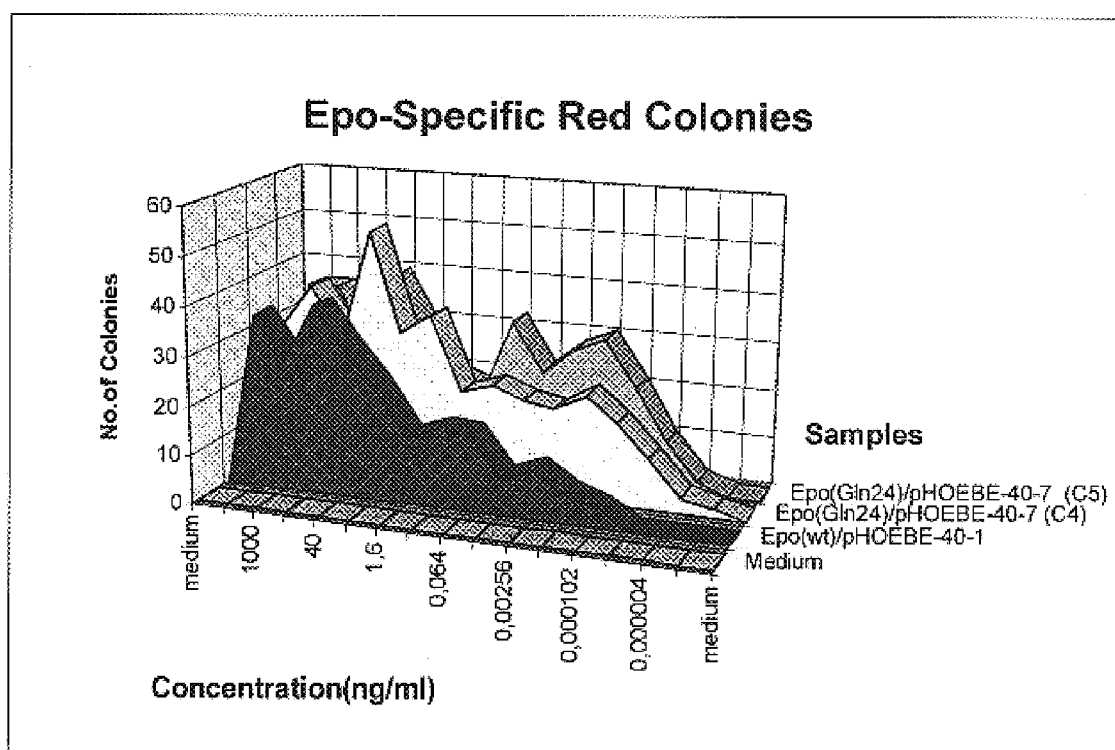

Human Epo has one O-linked (at Ser126 of SEQ ID NO: 1) and three N-linked glycosyl residues (at Asn 24, Asn 38 and Asn 83 of SEQ ID NO: 1), which are sialylated[1]. It has been demonstrated that proper sialylation of these sugar residues is important for the in vivo half-life and, subsequently, for the efficacy of Epo[2]. Furthermore, it has been demonstrated that different glycosylation sites of rhuEpo are glycosylated differently concerning the complexity of the sugar structures and sialylation[7,8]. The analysis of genetically engineered glycomuteins showed, that elimination of glycosylation site Asn24 of the rhuEpo molecule (SEQ ID NO: 1) resulting in the glycomutein rhuEpo (Gln24) (SEQ ID NO: 2) is advantageous for both expression and in vivo efficacy[4]. It has now been surprisingly found that rhuEpos that have a modified glycosylation profile in terms of sulfated N-glycan structures and N-glycan charge number per glycosylation site have an improved in-vivo half-life and biological activity compared to rhuEpo or any other rhuEpo glycomutein so far described[3,4]. The present invention is based on the finding that the glycosylation profile of the mutein rhuEpo (Gln24) (SEQ ID NO: 2) can even be improved by expression of the corresponding DNA sequence under the control of the regulatory elements of the Bovine Papillomavirus 1 (BPV-1) vector pHOEBE 40-7 in Chinese Hamster Ovary cell (CHO) cells. Although lacking one N-glycosylation site, the polypeptide (SEQ ID NO: 2) comprises a total charge number higher than rhuEpo (wt), and even higher than previously described rhuEpo (Gln24)[4,5,6], resulting in a significantly higher $Z^*$; see Table II of Example 9. The polypeptide of the invention has a high amount of sialylated/sulfated sugar structures per glycosylation site, reducing the clearance of the molecule by the liver-specific asialogalactosyl-receptors. Furthermore, the same biological effect of a certain dose of rhuEpo(wt) is obtained with a lower dose of the polypeptide of the invention; see FIG.1B. Additionally, as human urinary Epo was found to contain significant amounts of sulfated oligosaccharides[9] the polypeptide of the invention resembles more closely the human urinary Epo than any of the other rhuEpo so far available.

The potential exists, in the use of recombinant DNA technology, for the preparation of various derivatives of the polypeptide of the invention, variously modified by resultant single and/or multiple amino acid deletion(s), substitution (s), insertion(s), addition(s) and/or replacement(s), for example by means of side directed mutagenesis of the underlying DNA. Recombinant DNA technology is well known to those skilled in the art. Included is the preparation of derivatives retaining the primary structural confirmation of erythropoietin possessing the biological property of causing bone marrow cells to increase production of erythrocytes and red blood cells and to increase hemoglobin synthesis or iron uptake retaining the essential glycosylation profile, namely that greater than 5% of the N-glycan structures are sulfated and the ratio $Z^*$ of the total N-glycan charge Z to the number of N-glycosylation sites is greater than 170.

In a preferred embodiment the invention relates to the afore-mentioned polypeptide, wherein at least one of the consensus N-glycosylation sites is deleted and/or is replaced with (a) different amino acid(s).

In another preferred embodiment, at least one of the consensus N-glycosylation sites is added to the polypeptide as described above.

In a particularly preferred embodiment, the glycosylation site at the amino acid position 24 (Asn) of the amino acid sequence given in SEQ ID NO: 1 is deleted, preferably by replacing the amino acid Asn at position 24 of the amino acid sequence shown in SEQ ID NO: 1 with the amino acid Gln shown for example in the amino acid sequence of SEQ ID NO: 2.

As described above, the polypeptide of the invention has a ratio $Z^*$ of the total N-glycane charge Z to the number of N-glycosylation sites greater than 170. In a preferred embodiment $Z^*$ is greater than 180, e.g. 183, preferably greater than 190, e.g. 194.

Furthermore, the present invention relates to a DNA sequence encoding the amino acid sequence of the afore-described polypeptides operatively linked to regulatory elements of Bovine Papillomavirus 1 (BPV-1) which allow for the expression of said DNA in a eukaryotic host cell. Experiments which had been carried out in the scope of the present invention revealed that when the mutein rhuEpo (Gln24) is expressed in CHO cells via a BPV-1 expression system the glycosylation pattern is significantly different from mutein rhuEpo(Gln24) expressed in CHO cells via the pABE40-7 expression vector; see Table II, C3 and C4/C5. Using the BPV-1 expression system, rhuEpo(Gln24) comprises higher sialylation and a new quality of chargement through sulfatation; see Table II. Besides the expected recombinant protein, BPV-1 expression vectors are able to express several further functional activities, e.g. transacting factors and others, that can modulate the cellular activities of the host system. It is surprising, however, that it obviously can also modulate the pattern of posttranslational modifications, e.g. the glycosylation or sulfatation of rhuEpo (Gln24) in CHO cells.

In a preferred embodiment, the aforementioned DNA sequence further comprises regulatory elements of the metallothioneine 1 (MT-1) gene. Further examples of possible regulatory elements are viral regulatory elements such as SV40 promoter and enhancer elements.

The present invention also relates to vectors, preferably expression vectors, comprising a DNA sequence as described above.

In a preferred embodiment, the expression vector is BPV-1 vector pPHOEBE40-7 described in the examples hereinafter.

The present invention further relates to host cells comprising a DNA sequence or a vector of the invention. The DNA sequence or vector of the invention which is present in the host cell may either be integrated into the genome of the host cell or may be maintained in some form extrachromosomally. The host cell can be any eukaryotic cell, such as CHO, baby hamster kidney cell, C127I and others. Preferred host cells are CHO cells.

Another subject of the invention is a method for the production of the polypeptide of the invention having part or all of the primary structural conformation of erythropoietin possessing the biological property of causing bone marrow cells to increase production of reticulocytes and red blood cells and to increase hemoglobin synthesis or iron uptake, said method comprising culturing a host cell of the invention, and optionally isolating said polypeptide from the culture.

Depending on the specific constructs and conditions used, the polypeptide may be recovered from the cells, from the culture medium or from both. For a person skilled in the art it is well known that it is not only possible to express a native polypeptide but also to express the polypeptide as a fusion protein or to add signal sequences directing the polypeptide to specific compartments of the host cell, ensuring secretion of the polypeptide into the culture medium etc. Preferably, the polypeptide of the invention is purified by affinity chromatography, using a monoclonal antibody specific for the huEpo-receptor binding site on the rhuEpo molecule[10]. Such monoclonal antibodies can be obtained according to conventional methods known in the art.

Thus, the present invention also relates to the polypeptide obtainable by the afore-mentioned method. The polypeptide of the invention is characterized by its increased half-life and bioactivity in-vivo compared to the same polypeptide having part or all of the primary structural conformation of erythropoietin possessing the biological property of bone marrow cells to increase the production of reticulocytes and red blood cells and to increase hemoglobin synthesis or iron uptake but which does not have the advantageous glycosylation profile as described above for the polypeptide of the present invention.

Moreover, the present invention relates to a pharmaceutical composition comprising at least one of the afore-mentioned polypeptides, DNA sequences and/or vectors of the invention either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. The pharmaceutical compositions can be administered to the subject at a suitable dose. The dosage regimen will be determined by the attending physician considering the condition of the patient, the severity of the disease and other clinical factors. Suitable doses range, for example, from 1,000 to 10,000 units, preferably 3,000 to 6,000 units and are more preferably 4,000 units. Progress can be monitored by periodic assessment of hematocrit, number of reticulocytes, number of red blood cells, and the patient's general state of health. Administration of the suitable compositions may be effected by different ways, e.g. by intravenous, intraperetoneal, subcutaneous, intramuscular, topical or intradermal administration.

The invention also relates to a diagnostic composition comprising at least one of the afore-mentioned polypeptides, DNA sequences and/or vectors either alone or in combination, and optionally suitable means for detection. Said diagnostic composition may be used for methods for detecting anti-human Epo antibodies or Epo receptors. The polypeptide of the invention comprised in a diagnostic composition may be coupled to any reporter system such as peroxydase or 99 Tc.

In a further embodiment the invention relates to the use of at least one of the afore-mentioned polypeptides, DNA sequences and/or vectors either alone or in combination for the preparation of a pharmaceutical composition for treating all kinds of anaemia caused by a lack of erythropoietin to increase the overall number of functional red blood cells of an organism, e.g., in renal anaemia. For example, during dialysis, red blood cells can be destroyed so that dialysis patients can become anaemic. Since the kidneys of these patients are often insufficient and non-functional, a proper erythropoietin supply is not guaranteed so that dialysis patients need rhuEpo therapy to provide a sufficient rhuEpo level, which then is able to continuously replace the destroyed red blood cells.

In the pharmaceutical compositions and uses of the invention the polypeptide of the invention may be coupled covalently or non-covalently to carriers, e.g., keyhole limpet hemocyanine and/or any effector system such as ricin or 99 Tc.

The examples illustrate the invention.

Example 1

Construction of Expression Vector pHOEBE-40-7 (rhuEpo(Gln24))

For the expression of erythropoietin in CHO cells an expression system derived from the BPV-1 expression vector pCES was used[11]. To optimize the translational start site according to Kozak[12], an ACC Triplett was inserted directly upstream of the first ATG codon of the Epo coding sequence by site directed mutagenesis. Then rhuEpo(wt)-coding sequences of vector pCES (BamHI-BglII fragment) were exchanged by the Epo sequences with the optimal transcriptional start site, resulting in expression vector pHOEBE40-1. Alternatively, the sequence coding for mutein rhuEpo (Gln24), also including the Kozak sequence, was cloned into the expression vector, resulting in pHOEBE40-7. In further experiments the pABE40 expression vector system[4] was used for the expression in CHO cells. The mutein sequences and the Kozak sequence were obtained by site directed mutagenesis[13] and the sequences had been verified by sequence analysis. The BPV-1 expression system pHOEBE40-contains DNA fragments of different origin. The different elements are a) a SalI-EcoRI fragment of 2317 bp derived from plasmid pJYM[14], containing sequences of the bacterial plasmid pML-1, including the ampicillin resistance gene (Amp) and bacterial origin of replication (*E.coli* ORI);

b) an EcoR I-BamH I fragment of 2801 bp, containing the mouse metallothionein 1 (MT-1) promoter and the 3'non-coding region of the murine MT-1 gene, in the reverse orientation. Due to the cloning strategy, the two parts of the MT-1 gene, are separated by a short pBR322-derived sequence of 31 bp (Hind III-EcoR I) of vector pJYM[14];

c) a BamH I-Bgl II fragment of 766 bp, containing the rhuEpo(Gln24) c-DNA (E40-7)[4], and the upstream optimized translation start site.

d) a Bgl II - BamH I fragment of 242 bp containing the SV 40 late polyadenylation signal[15];

e) a BamH I-Sal I fragment of 7953 bp containing the total genomic sequence of the bovine papilloma virus BPV-1 (corresponding to the 100% BPV-1 genome BamH I-fragment)[16]. This sequence contains a eukaryotic origin of replication, located in a fragment of about 100 bp (7900 bp-52 bp of BPV-1 genome, adjacent to the Hpa I site at position 1). Furthermore, the sequence comprises open reading frames coding for BPV-1-specific replication factors, transcription factors and transforming factors. It is suggested that these factors are able to modulate posttranslational modification processes.

Example 2

Transfection of CHO dhfr⁻ Cells and Detection Transient Expression Levels

CHO dhfr⁻ cells were grown in Dulbecco's modified Eagle's medium (DMEM) containing 10% fetal calf serum (FCS). Transfections of CHO dhfr⁻ cells were carried out using the method according to Graham and Van der Eb[17]. Transient expression and secretion was analyzed 24, 48, and 72 hours after transfection of 10 μg/ml of rhuEpo expression vector DNA (pABE-40-7)[4]. In each transient expression experiment, vector p4EGD[18] carrying the coding sequence of a truncated human IgG$_1$ Fc (rhu IgG$_1$ Fc) under the control of the SV40 promoter[19,20] was cotransfected, and the expression rates of both rhuEpo and rhu IgG$_1$ Fc were determined using specific enzyme-linked immunoassays (EISAs)[21,10], respectively. The relative secretions of the rhuEpo muteins were standardized on the secretion rates of rhuEpo(wt) and rhu IgG$_1$ Fc (see Table I).

TABLE I

Transient Secretion of CHO-Derived rhuEpo Muteins

| Time (hours p.t.) | 1 rhuEpo Mutein | 2 Absolute Secretion (ng/ml) rhuEpo | | 3 Secretion (%) Relative to Fc | 4 Secretion (%) Relative to rhuEpo(wt) |
|---|---|---|---|---|---|
| | | rhuEpo | Fc | | |
| 24 | rhuEpo(wt) | 2.9 | 4.9 | 59.2 | 100.0 |
| | rhuEpo(Gln24) | 23.0 | 13.7 | 167.9 | 283.6 |
| 48 | rhuEpo(wt) | 7.2 | 14.0 | 51.4 | 100.0 |
| | rhuEpo(Gln24) | 53.0 | 21.0 | 252.4 | 491.0 |
| 72 | rhuEpo(wt) | 9.7 | 23.0 | 42.2 | 100.0 |
| | rhuEpo(Gln24) | 74.0 | 31.0 | 238.7 | 565.6 |

Transient transfectants were tested for expression of rhuEpo(wt) and rhuEpo(Gln24) relative to IgG$_1$ Fc fusion protein as a secreted reference protein post transfection (p.t.) at 24 h, 48 h and 72 h, respectively. The average values of triplicate determinations (n=3) of the absolute secretion levels from each transfection set were averaged. The variations of the triplicate values were below 5% for either rhuEpo/rhuEpo mutein secretion or rhuEpoRFc secretion (column 2). From these data the rhuEpo expression levels relative to IgG$_1$Fc (Fc, 100%) expression were calculated on a percent basis for each experiment (column 3). From these values, the rhuEpo(Gln24) secretion levels were estimated relative to rhuEpo(wt) on a percent basis for each experiment (column 4).

Example 3

Detection of Transient rhuEpo(wt), rhuEpo(Gln24) Mutein and rhuIgG$_1$ Fc Expression Levels Supernatants of transiently or stably transfected cultures were tested for rhuEpo(wt) or rhuEpo mutein content by a rhuEpo-specific ELISA[21,10]. Based on a polyclonal rabbit antiserum, this assay was carried out as follows: microtitration plates were coated overnight with 500 ng per ml of a rabbit anti-rhuEpo immunoglobulin fraction. Then the plates were washed three times with PBS containing 0.01% of Tween20 and air-dried at 37° C. Before use, the plates were saturated with PBS containing 0.05% (w/v) of bovine serum albumin (BSA). Then the plates were washed three times with PBS-Tween20 and incubated with the supernatant samples for 30 minutes. After washing for three times with PBS containing 0.05% (w/v) of BSA, bound rhuEpo or rhuEpo muteins were detected by peroxidase-labelled rabbit anti-rhuEpo immunoglobulin fraction (Ig-POD). After 30 min of incubation, the microtitration plates were washed and the remaining peroxidase activity, corresponding to captured rhuEpo, was developed, using tetramethylbenzidine (TMB) as a substrate. Then the reaction was stopped by addition of H$_2$SO$_4$, and the plates were measured in a Behring ELISA Processor II (Behringwerke AG, Marburg, FRG).

Supernatants of transiently transfected cell cultures were screened for the secretion of IgG$_1$Fc, to determine the relative secretion of the different rhuEpo muteins. For this, microtitration plates were coated with goat anti-human Fc polyclonal immunoglobulin fraction. After washing and saturation (see above), the plates were incubated with the supernatants for 1 hour. Then the captured IgG$_1$Fc molecules were detected by goat anti-human Fc antibodies, labelled with peroxidase (POD) as described above.

Example 4

Production of Stable rhuEpo(Gln24) Mutein Expressing Cell Clones

Cell clones secreting rhuEpo(Gln24) mutein were obtained by cotransfection of the vector pSV2 dhfr expressing the dihydrofolatereductase gene, providing resistance against methotrexate[18], together with expression vectors pABE40-1, pABE40-7, pHOEBE40-1, or pHOEBE40-7, respectively. After transfection the cultures were selected in the presence of methotrexate. After a period of two to three weeks, cell colonies grew out and single cell clones were cloned by use of cloning cylinders or according to the limiting dilution method. The production of rhuEpo(Gln24) was analyzed as described in Example 2.

Example 5

Upscaling of Production Cell Clones

Cell clones suitable for production were further cultivated and finally expanded to roller bottle cultures. To produce erythropoietins, cells from the respective seed lots were expanded in roller bottles to confluence. Then the growth medium was replaced by serum-free DMEM, which was harvested at the end of the production phase.

Example 6

Purification of rhuEpo(Gln24)

Purified rhuEpo and glycomuteins were obtained by affinity chromatography using monoclonal antibody 146/0056[10] This antibody was covalently coupled to sepharose CL4B (Pharmacia, Uppsala, Sweden) according to Fibi[10]. After elution at pH 2.5 into 1 ml of 1 M Tris-HCl, pH 9.5, the samples were dialyzed against PBS pH 7.0. The protein concentration was calculated from the O.D. 280 nm, and the purity of the preparation was controlled visually after separation in a polyacrylamide gel and subsequent silver staining (Phast System, Pharmacia).

Example 7

SDS-Page and Silver Staining

SDS-PAGE and Western blotting procedures were carried out as described recently[10], using the Phast System, except that rainbow marker proteins and a gold-labelled-antibody procedure (both from Amersham-Buchler, Braunschweig, FRG) were used.

Example 8

Human Erythroid Precursor Colony Assay

Suspensions of human bone marrow cells were prepared from bone marrow specimens in phosphate buffered saline. Gradient-purified interphase cells of the suspensions were harvested after centrifugation at 2200 rotations per minute for 25 min at 12° C. The cells were washed three times, resuspended in MEM-alpha medium with supplements and certomycin as an antibiotic. The cell number was adjusted to $1.1 \times 10^6$/ml, and the cells were mixed with 4 ml rhuEpo Medium (19,1 ml FCS/15,2 ml Transferrin/BSA/FeCI$_3$/13,7 ml MEM-alpha medium), and 0,7 ml Agar (about 70° C.). 200 µl of the agar cell suspension were added per well to 24 well tissue culture plates, containing dilutions of the test samples. The cultures were mixed with the test samples and incubated for 14 days at 37° C in an atmosphere containing 7% $CO_2$ and 10% $O_2$.

Example 9

Glycoanalysis

The liberation by PNGase F of the N-glycans of rhuEpo was performed as described by Nimtz.[7] The liberated N-glycan pools were measured by high-pH anion-exchange chromatography with pulsed amperometric detection (HPAE-PAD), using the set-up and the optimized standard gradient "S" for sialylated glycans previously described[22]. The hypothetical N-glycan charge Z was determined as described by Hermentin[23,24]. In brief, the hypothetical N-glycan charge of the rhuEpo samples was gained by i) liberating the N-glycan-pool of the glycoprotein via PNGase F
 ii) measuring the N-glycan pool via HPAE-PAD
 iii) calculating the percentage of the areas (A) of the groups of peaks, separated by charge,
 iv) multiplying the area% of the peak-groups in the neutral (asialo-, as), monosialo-(MS), disialo- (DiS), trisialo- (TriS), tetrasialo- (TetraS) and pentasialo (PentaS) region by zero (asialo), 1 (MS), 2 (DiS), 3 (TriS), 4 (TetraS), and 5 (Sulfated), respectively, and
 v) summarizing the respective products.
    Thus, Z was defined as the sum of the products of the respective areas (A) in the asialo (as), monosialo (MS), disialo (DiS), trisialo (TriS), tetrasialo (TetraS) and sulfated region, each calculated as the percentage of the total peak area set equal to 100%, and each multiplied by the corresponding charge:

$$Z = A_{(as)}*0 + A_{(MS)}*1 + A_{(DiS)}*2 + A_{(TriS)}*3 + A_{(TetraS)}*4 + A_{(Penta\ S\ or\ Sulfated)}*5$$

vi) dividing Z through the number of glycosylation sites to create Z*. Z* gives an estimate of the number of charges per N-glycosylation site and, thus, of the grade of chargement of a glycosylation site.

The results of the glycoanalysis of rhuEpo so far commercially available and the rhuEpo of the invention (column C4 and C5) are compared in Table II.

TABLE II

Comparison of the glycoylation profiles of different recombinant human erythropoietins

| area of intergration (peak group) | Organon rhuEpo (CHO) pABE-40-like | | Amgen* rhuEpo (CHO) pABE-40-like | | Boehringer rhuEpo (CHO) pABE-40 like peak group | | Behring-Mutein rhuEpo (Gln24) (CHO) pABE-40-7 C3 peak group | |
|---|---|---|---|---|---|---|---|---|
| | peak group area (%) | charge number share | peak group area (%) | charge number share | area (%) O950579 K.D07 | charge number share | area (%) O950576 K.D04 | charge number share |
| asialo | | | | | | | 3.1 | 0 |
| monosialo | | | | | | | 6.1 | 6.0 |
| disialo | 15 | 30.0 | 6.4 | 12.8 | 5.4 | 10.7 | 11.3 | 23.0 |
| trisialo | 32 | 96.0 | 20.7 | 62.1 | 25.5 | 76.5 | 23.7 | 71.0 |
| tetrasialo | 40 | 160.0 | 72.9 | 291.6 | 69.2 | 276.6 | 55.9 | 223.0 |
| sulfated | | | n.d. | | n.d. | | 0.0 | 0 |
| N-glycan charge number Z (total) | (a) | 286 | (b) | 367 | | 364 | | 323 |
| Z* | | 95.3 | | 122.3 | | 121.3 | | 162.5 |

TABLE II-continued

Comparison of the glycoylation profiles of different recombinant human erythropoietins

| | Behring-Mutein rhuEpo (Gln24) (CHO) pHOEBE-40-7 | | | | Merckle rhuEpo (BHK) pABE-40-like | | | |
| --- | --- | --- | --- | --- | --- | --- | --- | --- |
| | C4 peak group | | C5 peak group | | | | Nimtz[7] | |
| area of intergration (peak group) | area (%) O950576 K.D04 | charge number share | area (%) o950546 D.K20 | charge number share | peak group area (%) | charge number share | peak group area (%) | charge number share |
| asialo | | | | | | | | |
| monosialo | 2.8 | 2.8 | 1.8 | 1.8 | 4.7 | 4.7 | n.d. | |
| disialo | 3.2 | 6.3 | 8.6 | 17.3 | 14.5 | 29.0 | 21.1 | 42.2 |
| trisialo | 13.8 | 41.4 | 20.2 | 60.6 | 33.9 | 101.7 | 35.0 | 105.0 |
| tetrasialo | 64.0 | 256.0 | 60.6 | 242.4 | 46.8 | 187.2 | 40.9 | 163.6 |
| sulfated | 16.2 | 81.2 | 8.7 | 43.5 | | | | |
| N-glycan charge number Z (total) | | 388 | | 366 | (c) | 323 | (d) | 311 |
| Z* | | 194 | | 183 | | 107 | | 103 |

(a) calculated from Hokke[25]
(b) calculated from Watson[26]
(c) average of 4 different batches; 1 HPAE-PAD run, each
(d) calculated from Nimtz[7]
Z* Total N-glycan charge number Z/number of N-glycosylation sites.
n.d. not determined The carbohydrate analysis of rhuEpo, originally described by Sasaki et al.[1] and Takeuchi[27] for rhuEpo (CHO) and by Tsuda[28] for rhuEpo (BHK), has recently been extended by studies of Hokke[25], Watson[26] (for CHO-rhuEpo), and Nimtz[7] (for BHK-rhuEpo). According to a new method, the hypothetical N-glycan charge Z can be determined as described by Hermentin[23,24]. It has been demonstrated that this parameter gives an excellent estimate of the amount of undersialylated N-glycans to properly sialylated N-glycans. As the glycans of rhuEpo are known to consist of mainly tetraantennary structures with 0–3 LacNAc repeats, Z should amount to a hypothetical N-glycan charge number between 300 and 400. Indeed, the N-glycan charge of CHO-rhuEpo (Boehringer Mannheim) was determined to Z=364 +/-2 (CV=0.6%) (n=6; three different experiments with 2 HPAE-PAD runs, each), and the N-glycan charge of BHK-rhuEpo (Merckle) was determined to Z=323 +/-2 (CV=0.7%) (n=4; four different lots; 4 different experiments; 1 HPAE-PAD run, each); see Table II[24]. Thus, the smaller Z value of the BHK-rhuEpo from Merckle clearly reflected the greater share of undersialylated N-glycans: 34% of the N-glycans were missing one and 12% of the N-glycans were missing two terminal sialic acid residues; the structures consisted of 40.9 % tetrasialylated, 35.0% trisialylated and 21.1% disialylated structures (Nimtz.[7]). These data from the literature allowed to calculate the N-glycan charge to Z=311, which is in good agreement (deviation<4%) with the N-glycan charge determined according to Eq. 1, supra, i.e., Z=323, using the same rhuEpo (BHK) from Merckle (see Table II). In the CHO-rhuEpo from Amgen the major (>95%) di-, tri- and tetra-antennary structures were fully sialylated[26]. Their separation according to charge of the PNGase F-released N-glycans (using a Glycopak DEAE column) allowed to calculate the N-glycan charge to Z=367, which is in excellent agreement with the glycan charge of the rhuEpo (CHO) from Boehringer Mannheim, used in this study (Z=364, see Table II). In contrast, the study of Hokke et al.[25], investigating CHO-rhuEpo from Organon Teknika, showed that 18–20% of the N-glycans were missing one, and 3% of the N-glycans were missing two sialic acid residues. Their structural analysis enabled to calculate the N-glycan charge to Z=286, which is significantly smaller than the CHO-rhuEpo from Amgen (Z=367) or Boehringer (Z=364); see Table II[24].

References

1. Sasaki, J. Biol. Chem. 262 (1987),12059
2. Goldwasser, J. Biol. Chem. 249 (1974), 4202
3. Delorme, Biochemistry 31 (1992), 9871
4. Fibi, Blood 85 (1995),1229
5. U.S. Pat No. 5,457,089
6. EP0,409,113B1
7. Nimtz, Eur. J. Biochem. 213 (1993), 39
8. Sasaki, Biochemistry 27:8618,1988
9. Strickland, J. Cell. Biochem. Suppl. 16D (1992), P324,
10. Fibi, Blood 81 (1993), 670
11. Fibi, Appl.Microbiol.Biotechnol., 35 (1991), 622
12. Kozak, Cell, 44 (1986), 283
13. Kramer, Nucl. Acids Res. 12 (1984), 9441
14. Lusky, Nature 293 (1981), 79
15. Fiers, Nature 273 (1978), 113–120,
16. Chen, Nature 299 (1982), 529
17. Graham, Virology 52 (1973), 456
18. Lee, Nature 294 (1981), 228
19. Aruffo, Cell 61 (1990), 1303
20. Zettlmeiβl, DNA and Cell Biol. 9 (1990), 347
21. Fibi, Blood 77 (1991), 1203
22. Hermentin, Anal. Biochem. 203 (1992), 281
23. PCT/EP96/02319
24. Hermentin, Glycobiology 6 (1996)
25. Hokke, Eur. J. Biochem. 228 (1995), 981
26. Watson, Glycobiology 4 (1994), 227
27. Takeuchi, J. Biol. Chem. 263 (1988), 3657
28. Tsuda, Biochemistry 27 (1988), 5646

What is claimed is:

1. A method for the production of a polypeptide, said method comprising culturing, under conditions which allows for the expression of a DNA encoding amino acid sequence SEQ ID NO:2 in an eukaryotic host cell, wherein said DNA is in a vector pPHOEBE-40-7, and optionally isolating said polypeptide from the culture.

2. The method of claim 1, wherein said eukaryotic host cell is a Chinese Hamster Ovary cell.

3. A polypeptide obtained by the method of claim 1.

4. An erythropoietin polypeptide produced by expressing DNA encoding amino acid sequence SEQ ID NO:2 in a host cell, wherein said DNA is in the vector pPHOEBE-40-7 and said host cell is a Chinese Hamster Ovary cell, and wherein the erythropoietin polypeptide consists of the amino acid sequence of SEQ ID NO:2.

5. A pharmaceutical composition comprising the polypeptide of claim 3 and a pharmaceutical acceptable carrier.

6. A composition for diagnosing anemia, said composition comprises the polypeptide of claim 3.

7. A method for treating anemia caused by a lack of erythropoietin, comprising administering the polypeptide of claim 3 to a subject suffering from the anemia in need thereof and reducing the anemia caused by a lack of erythropoietin.

* * * * *